United States Patent
Rehnstrom

(10) Patent No.: US 8,025,405 B2
(45) Date of Patent: Sep. 27, 2011

(54) EYE TRACKING ILLUMINATION

(75) Inventor: Bengt Rehnstrom, Vasterhaninge (SE)

(73) Assignee: Tobil Technology AB, Danderyd (SE)

( * ) Notice: Subject to any disclaimer, the term of this patent is extended or adjusted under 35 U.S.C. 154(b) by 233 days.

(21) Appl. No.: 12/447,871

(22) PCT Filed: Nov. 29, 2007

(86) PCT No.: PCT/SE2007/001058
§ 371 (c)(1),
(2), (4) Date: Apr. 29, 2009

(87) PCT Pub. No.: WO2008/066460
PCT Pub. Date: Jun. 5, 2008

(65) Prior Publication Data
US 2010/0066975 A1    Mar. 18, 2010

Related U.S. Application Data

(60) Provisional application No. 60/869,470, filed on Dec. 11, 2006.

(30) Foreign Application Priority Data

Nov. 29, 2006    (SE) ...................... 0602545

(51) Int. Cl.
*A61B 3/10*    (2006.01)
*A61B 3/14*    (2006.01)
(52) U.S. Cl. ....................................... 351/210
(58) Field of Classification Search ................. 351/205, 351/208–209, 210
See application file for complete search history.

(56) References Cited

U.S. PATENT DOCUMENTS 4,889,422 A * 12/1989 Pavlidis ..................... 351/210
5,889,577 A * 3/1999 Kohayakawa ............... 351/211

FOREIGN PATENT DOCUMENTS

| EP | 1114608 | 7/2001 |
| WO | WO99/27412 | 6/1999 |
| WO | WO2005/046465 | 5/2005 |
| WO | WO2006/016366 | 2/2006 |

OTHER PUBLICATIONS

International Search Report for PCT/SE2007/001058, dated Feb. 11, 2008.
International Preliminary Report on Patentability for PCT/SE2007/001058, dated Jun. 3, 2009.

* cited by examiner

*Primary Examiner* — Rick Mack
*Assistant Examiner* — Dawayne A Pinkney
(74) *Attorney, Agent, or Firm* — Moore & Van Allen PLLC; W. Kevin Ransom; Patrick B. Horne

(57) ABSTRACT

The invention relates to automatic eye tracking, wherein at least one imaging device (150) registers sequential image data ($D_{EYE}$) representing at least one eye (181; 182) of a subject (180). A processing unit (170) receives the image data ($D_{EYE}$), and based thereon, produces a position estimate of the at least one eye (181; 182). The processing unit (170) also produces a control signal ($D_{ILL}$) which is received by at least one light source (140). The at least one light source (140), in turn, emits at least one light beam (L) being variable, such that a spatial location of an illumination area ($A_{ILL}$) towards which at least one light beam (L) is directed depends on the characteristics of the control signal ($C_{ILL}$). Specifically, the processing unit (170) produces the control signal ($C_{ILL}$) so that the illumination area ($A_{ILL}$) includes a position estimate of the at least one eye (181; 182).

20 Claims, 3 Drawing Sheets

EYE TRACKING ILLUMINATION

FIELD OF THE INVENTION

The present invention relates generally to automatic determination and tracking of the positions of a person's eyes. More particularly the invention relates to systems, methods, computer programs, and/or computer readable media for automatically registering and tracking a respective position of at least one eye (181; 182) of a subject.

BACKGROUND OF THE INVENTION

The concept of eye tracking is well known in the art and a number of different techniques have been developed for accomplishing automatic eye and gaze tracking. In the area of remote, non-obtrusive eye tracking, the most commonly used designs are based on pupil center corneal reflection (PCCR) methods. The basic idea behind this approach is to use at least one light source (e.g. infrared), and by means of a camera, capture a series of images of the eye. In each image the light source's refection (the glint) in the cornea and the pupil are identified. A vector defined from the glint to the center of the pupil is then used to estimate the eye's gaze direction.

However, to ensure adequate illumination of the subject's eyes a relatively high light power is required. This, in turn, results in comparatively high energy consumption. Moreover, it becomes necessary to provide the light source, or the unit into which the light source is integrated with resourceful cooling. The energy consumption and the heat dissipation is two-fold problematic.

Namely, due to the high power requirements, standard computer output interfaces (e.g. of USB format (USB—Universal Serial Bus)) cannot normally be used to supply power to the eye tracker. Furthermore, the high temperatures caused by the light source generally shorten the expected life of the electronic components included in the eye tracker. These problems can be alleviated somewhat by allocating a small view angle to the camera, so that the light source only needs to illuminate a relatively small spatial sector. Nevertheless, this causes new problems, since then the subject's eyes are restricted to a fairly small space to enable automatic eye tracking.

SUMMARY OF THE INVENTION

The object of the present invention is therefore to provide a power efficient and robust solution, which solves the above problems and thus offers a reliable automatic eye tracking in respect of a subject located within a relatively large operation space.

According to one aspect of the invention, the object is achieved by the system as initially described, wherein the at least one light source is adapted to vary a spatial location of an illumination area towards which at least one light beam from the at least one light source is directed. The at least one light source is adapted to receive a control signal, and direct the at least one light beam towards an illumination area specified by the control signal. The processing unit is adapted to produce the control signal based on the position estimate of the at least one eye, such that the illumination area includes the position estimate, either of at least one eye actually registered by the at least one imaging device, or of an expected eye location being based on previously registered images of the at least one eye.

This system is advantageous because the proposed adaptive direction of the illumination allows a large operating space while maintaining a relatively low energy consumption. The low energy requirements, in turn, render it possible to supply power to the system via a conventional computer interface, for instance of USB format. Hence, the solution is highly flexible and convenient to implement.

According to one preferred embodiment of this aspect of the invention, the at least one light source includes a plurality of light emitting elements that are individually controllable in response to the control signal. Hence, the light being emitted towards the subject can be efficiently controlled.

According to another preferred embodiment of this aspect of the invention, the light emitting elements are arranged in an array, which has a first number of rows of elements and a second number of columns of elements. Namely, such a configuration renders it easy to control the illumination to a designated area.

According to a further preferred embodiment of this aspect of the invention, the at least one light source includes at least one collimating lens element adapted to influence the light emitted from the light emitting elements, such that the light from a first element is directed towards a first portion of the illumination area and the light from a second element is directed towards a second portion of the illumination area. Hence, a group of light emitting elements can be used to jointly illuminate a designated area.

According to another preferred embodiment of this aspect of the invention, as an alternative or a complement to the above embodiment, the light emitting elements are arranged with different orientations relative to one another. Here, a first element has a first principal light emitting axis having a first angle in a first dimension towards a normal plane of the array, and a second element has a second principal light emitting axis whose angle towards the normal plane is different from the first angle at least in the first dimension.

According to yet another preferred embodiment of this aspect of the invention, the at least one light source is tiltable around at least one axis in response to the control signal, such that the illumination area is adjustable in at least one dimension. Alternatively, the at least one light source is configured to emit light towards at least one mirror being tiltable around at least one axis in response to the control signal, such that the illumination area is adjustable in at least one dimension. In either case, a projection of a light line, or a light point can be efficiently controlled to follow the movements of a subject's eyes.

According to a further preferred embodiment of this aspect of the invention, the control signal is further adapted to, for each element of the light emitting elements, specify at least one on-period during which light shall be emitted and at least one off-period during which no light shall be emitted. Hence, the light being emitted towards the subject can be efficiently controlled, for example such that the light is emitted during the exposure time of the at least one imaging device.

According to another preferred embodiment of this aspect of the invention, the processing unit is adapted to receive an input parameter, and in response thereto, set the on- and off-periods of the control signal. Thereby, the light emission can be conveniently controlled.

According to yet another preferred embodiment of this aspect of the invention, each of the at least one light emitting element of the at least one light source is controllable in response to the control signal, such that an intensity of the light emitted from a given element is variable depending on the characteristics of the control signal. For example, the control signal may specify a light intensity parameter, which designates a power of the light to be emitted during the on-period. The light intensity parameter may either represent a constant light intensity throughout the on-period, or an intensity value that varies during this period. Thus, further adjustment options for the light emission are provided.

According to another aspect of the invention the object is achieved by the method as initially described, wherein the at least one light source is adapted to vary a spatial location of an illumination area towards which at least one light beam from the at least one light source is directed. The method involves receiving a control signal, and directing the at least one light beam from the at least one light source towards an illumination area in response to the control signal. The control signal is produced in the processing unit based on the position estimate of the at least one eye, such that the illumination area includes the position estimate.

The advantages of this method, as well as the preferred embodiments thereof, are apparent from the discussion hereinabove with reference to the proposed system.

According to a further aspect of the invention the object is achieved by a computer program, which is loadable into the internal memory of a computer, and includes software for controlling the above proposed method when said program is run on a computer.

According to another aspect of the invention the object is achieved by a computer readable medium, having a program recorded thereon, where the program is to control a computer to perform the above proposed method.

Further advantages, advantageous features and applications of the present invention will be apparent from the following description and the dependent claims.

BRIEF DESCRIPTION OF THE DRAWINGS

The present invention is now to be explained more closely by means of preferred embodiments, which are disclosed as examples, and with reference to the attached drawings.

DESCRIPTION OF PREFERRED EMBODIMENTS OF THE INVENTION

Figure 1:
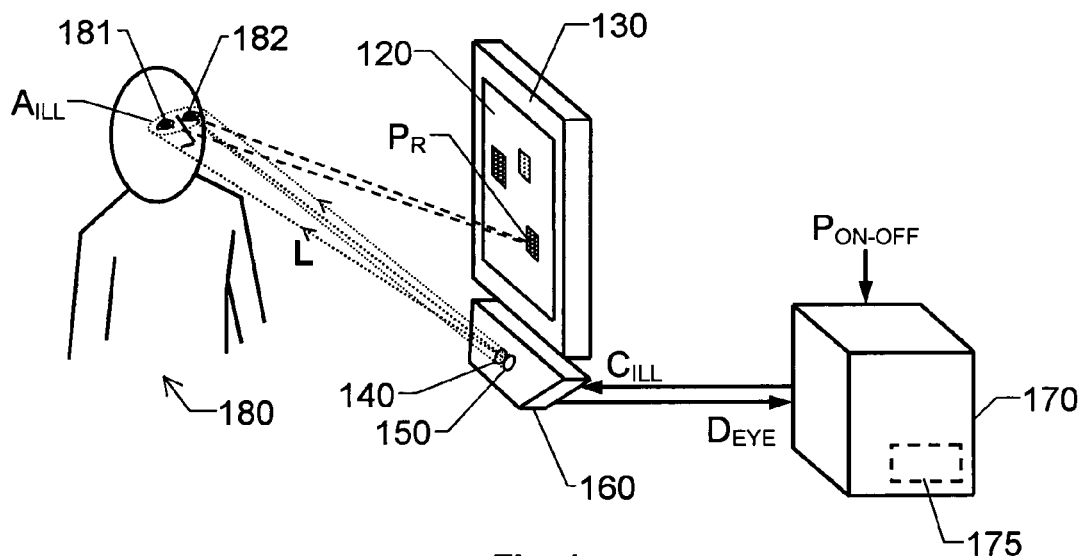
FIG. 1 shows an overview picture of a system according to one embodiment of the invention.

We refer initially to FIG. 1, which shows an overview picture of a system according to one embodiment of the invention. The system is adapted to automatically register and track a respective position of at least one eye 181 and 182 of a subject 180. Preferably, the system is further adapted to determine a gaze direction of the subject 180, so that a point of regard $P_R$ on for example a computer screen 120 can be derived. Thereby, the subject 180 may control a computer apparatus associated with the screen 120 in response to a movement sequence of the point of regard $P_R$.

The proposed system includes at least one imaging device 150, e.g. in the form of a video camera; at least one light source 140 and a processing unit 170.

The imaging device 150 is adapted to register sequential image data $D_{EYE}$ representing the at least one eye 181 and 182 respectively. The processing unit 170 is adapted to receive the image data $D_{EYE}$, and based thereon produce a position estimate of the at least one eye 181 and 182 respectively.

The light source 140, which is arranged to illuminate the subject 180, has a well-defined position relative to the imaging device 150. Here, the light source 140 is co-located with the imaging device 150 in an eye tracking unit 160 disposed proximate to the above-mentioned screen 120. For instance, the eye tracking unit 160 may be attached to a frame 130 of the screen 120. Moreover, the light source 140 is adapted to vary a spatial location of an illumination area $A_{ILL}$ towards which at least one light beam L from the at least one light source 140 is directed. Specifically, the light source 140 is adapted to receive a control signal $C_{ILL}$ from the processing unit 170 and direct the at least one light beam L towards an illumination area $A_{ILL}$ that is specified by the control signal $C_{ILL}$.

The processing unit 170, in turn, is adapted to produce the control signal $C_{ILL}$ based on the position estimate of the at least one eye 181 and 182 respectively, such that the illumination area $A_{ILL}$ includes the position estimate. As will be discussed below with reference to FIG. 5, the position estimate may either be given by actually registered sequential image data $D_{EYE}$ that include a representation of at least one eye, or the position estimate may represent an expected eye location that is based on previously registered sequential image data $D_{EYE}$. Furthermore, the processing unit 170 preferably includes, or is associated with, a computer readable medium 175 (e.g. a memory module) having a program recorded thereon, where the program is adapted to make the processing unit 170 control the at least one light source according to the above-described procedure.

Figure 2:
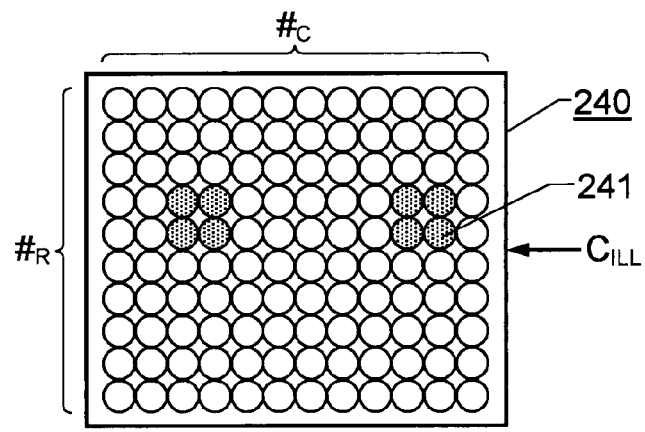
FIG. 2 illustrates an array of light emitting elements included in a proposed light source according to one embodiment of the invention.

FIG. 2 illustrates an array 240 of light emitting elements included in the proposed light source 140 according to one embodiment of the invention. The array 240 includes a first number $\#_R$ of rows of elements (say 10) and a second number $\#_C$ of columns of elements (say 12). The array 240 has an input via which the control signal $C_{ILL}$ can be received. The array 240 is further adapted to control the light emitting elements in response to the control signal $C_{ILL}$, such that one or more groups of elements are selectively lit up. For example, as illustrated in FIG. 2, the control signal $C_{ILL}$ may control the array 240 in such a manner that two groups of four light emitting elements 241 each emit light, and thus direct a respective light beam L towards a designated illumination area $A_{ILL}$ on the subject 180.

The elements of the array 240 are preferably represented by light emitting diodes (LEDs). These elements may be surface mounted onto a printed circuit board (or substrate) to form the array 240. Alternatively, the light emitting elements may be through-hole mounted LEDs that are soldered, or wire-wrapped, onto a circuit board. In the former case, the LEDs normally have a relatively wide light-radiation lobe (say 90°-100°, whereas in the latter case, each LED usually is provided with a lens element, which reduces the width of the light-radiation lobe (to say) 5°-10°. This will be discussed further below with reference to FIGS. 3a and 3b.

Figure 3A:
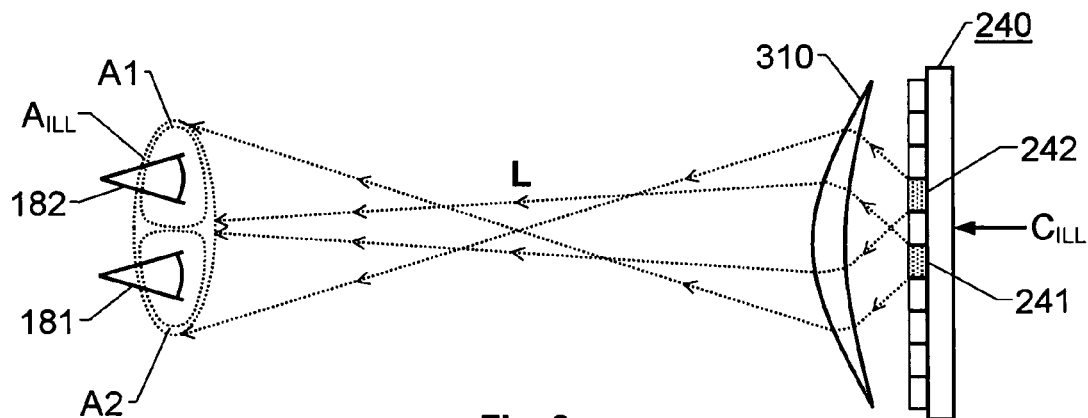
FIGS. 3a-d illustrate different configurations of the light emitting elements and light sources according to embodiments of the invention.

FIG. 3a illustrates a configuration of light emitting elements 241, 242 in an array 240 of a light source according to a first embodiment of the invention. In this embodiment, the light source includes a collimating lens element 310, which is mounted in front of the array 240 (i.e. between the light emitting elements 241, 242 and the intended illumination area $A_{ILL}$). The lens element 310 is adapted to influence light L emitted from the elements 241 and 242 such that an intended area $A_{ILL}$ is illuminated, i.e. an area $A_{ILL}$ including a respective position estimate of the at least one eye 181 and 182 of a subject 180. Specifically, the collimating lens element 310 is adapted to influence the light L, such that light emitted from a first element 241 is directed towards a first sub-portion A1 of the illumination area $A_{ILL}$. Analogously, light emitted from a second element 242 is directed towards a second sub-portion A2 of the illumination area $A_{ILL}$. Hence, the elements 241 and 242 jointly illuminate the area $A_{ILL}$.

Naturally, more than one collimating lens element 310 may be included in the light source. Moreover, for compactness, one or more of these lens elements may be represented by a so-called Fresnel lens.

The light emitting elements 241, 242 of the array 240 in the embodiment of the invention illustrated in FIG. 3a are preferably represented by LEDs that are surface mounted onto a printed circuit board/substrate. This type of elements normally have relatively wide light-radiation lobes (in the order of 90°) and therefore a focusing element, such as the proposed collimating lens, may be especially useful.

Figure 3B:
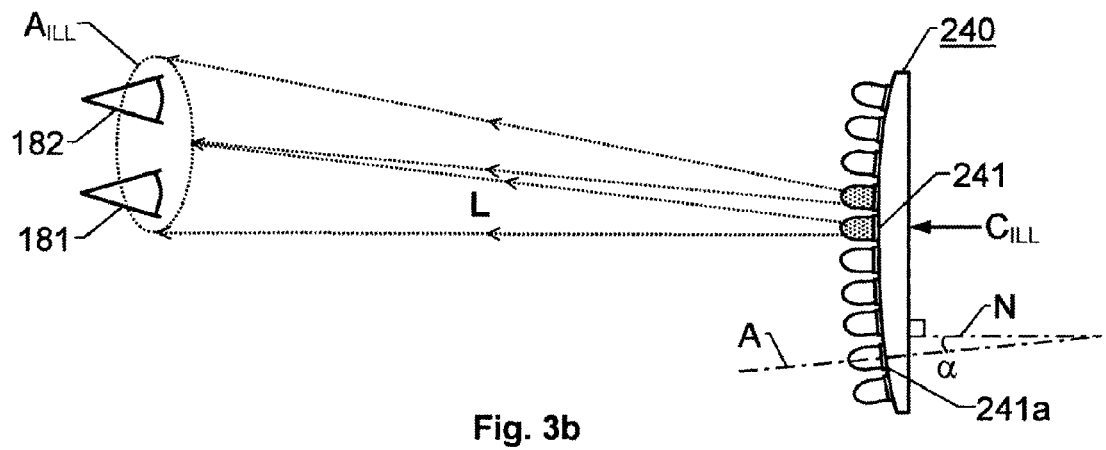

FIG. 3b illustrates a configuration of light emitting elements 241, 241a in an array 240 of a light source according to a second embodiment of the invention. Here, the light emitting element may be organized in essentially the same manner as in FIG. 3a, for instance in rows and columns, or concentrically. However, in the embodiment illustrated in FIG. 3b, the light emitting elements are arranged with different orientations relative to one another. This means that a first element 241a has a first principal light emitting axis A with a first angle α in a first dimension towards a normal plane N of the array 240. A second element 241, however, has a second principal light emitting axis whose angle towards the normal plane N is different from the first angle α at least in the first dimension. Consequently, provided that the first and second light emitting elements 241a and 241 have essentially identical optical properties, these element will emit light in different directions with respect to the first dimension, where the direction difference is given by the angular difference between the elements' principal light emitting axes. Naturally, the light emitting elements of the array 240 may have principal axes that differ from one another in more than one dimension, for instance both relative to the extensions of the rows and the columns in the array 240. Moreover, it is not excluded that two or more elements in the array 240 have identical axes, i.e. have exactly the same orientation.

The light emitting elements 241a, 241 of the array 240 in the embodiment of the invention illustrated in FIG. 3b are preferably represented by LEDs that are through-hole mounted and soldered, or wire-wrapped, onto a circuit board. This type of elements are normally provided with a respective lens element, and therefore have relatively narrow light-radiation lobes (in the order of 10°. Hence, these elements are suitable for direct illumination of the designated area $A_{ILL}$.

As an alternative, or a complement, to the above-mentioned embodiments, at least one transparent or reflecting grating element may be used in combination with a careful selection of the wavelength of the emitted light in relation to the geometric properties of the grating. Namely thereby, the light may be directed towards a designated illumination area as the result of constructive interference between different light beams having passed the grating. Hence, in this embodiment, the characteristics of the control signal $C_{ILL}$ determine the wavelength of the emitted light, and/or the geometric properties of the grating.

As yet another alternative, reflector-based optics may be employed in the light source 140 to direct the light beam L towards the designated illumination area $A_{ILL}$. For example, a so-called line laser, or an array of LEDs, may be used to emit light. Either the line laser (the array of LEDs) is tiltable around an axis being parallel to the extension of the line laser (the array of LEDs), or the line laser (the array of LEDs) is configured to emit light towards an elongated mirror with a concave cross section, which is tiltable around an axis being essentially parallel to both the mirror's elongation and the light line generated by the laser (the LEDs).

Figure 3C:
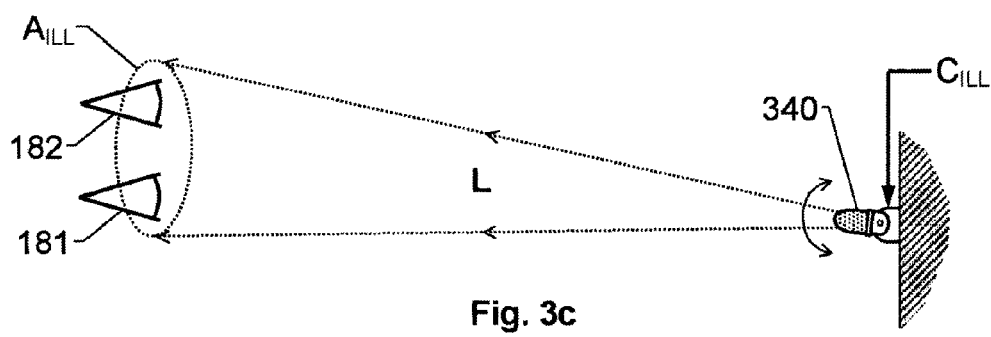
Figure 3D:
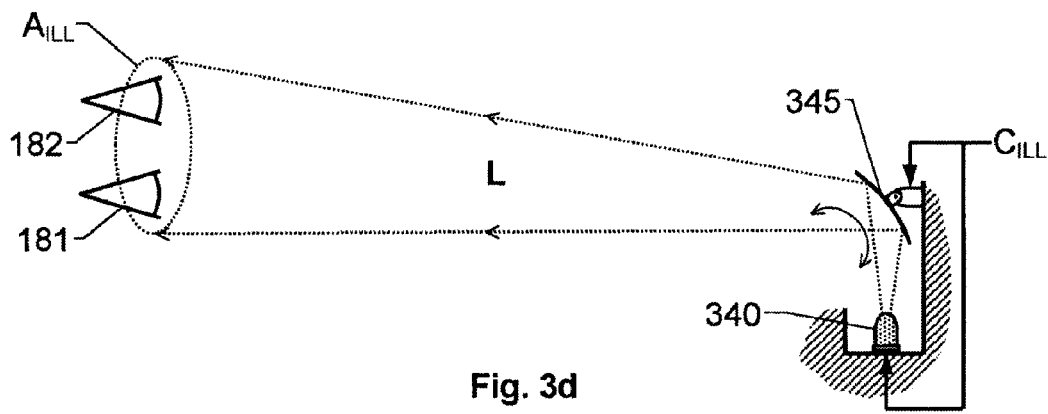

FIG. 3c illustrates an embodiment of the invention according to the former alternative, i.e. where the light source 340 is tiltable in response to the control signal $C_{ILL}$. FIG. 3d, on the other hand, illustrates an embodiment of the invention according to the latter alternative, i.e. where the light source 340 is fixed, however a mirror 345 in front of the light source 340 is tiltable in response to the control signal $C_{ILL}$.

In both above cases, a projection of a light line can be repositioned in a dimension being traverse to the tilt axis, and thereby for instance follow any vertical movements of a subject's pair of eyes.

For even more focused illumination of the designated area $A_{ILL}$, a single-point laser (or LED) may be used, which either in itself is adjustable in two dimensions, or a circular concave mirror in front thereof is adjustable in two dimensions. Typically, the adjustment axes are here perpendicular to one another. Hence, a projection of a light point can be repositioned to any point in a two-dimensional plane, and thereby follow any spatial movements of a subject's eyes.

Figure 4:
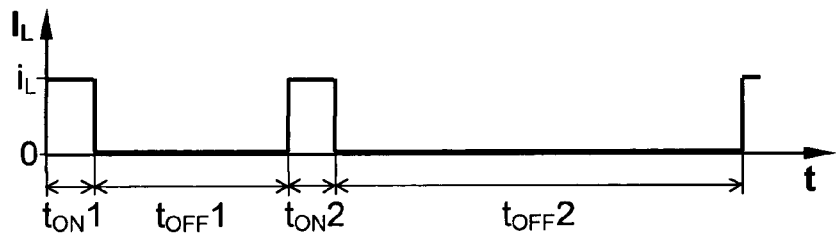
FIG. 4 illustrates a format of the control signal according to one embodiment of the invention.

FIG. 4 shows a diagram, which illustrates a format of the control signal $C_{ILL}$ according to one embodiment of the invention. The vertical axis of the diagram expresses an intensity $I_L$ of the light L to be emitted from a particular light emitting element of the proposed light source 140, and the diagram's horizontal axis represents time t.

In this case, it is presumed that the light source 140 includes a plurality of light emitting elements, and that these elements are controllable in response to the control signal $C_{ILL}$, either individually or in clusters of two or more elements. The control signal $C_{ILL}$ specifies on-periods during which light L shall be emitted from the element in question. The control signal $C_{ILL}$ likewise specifies off-periods during which no light shall be emitted. Here, a first on-period $t_{ON}1$ starts at t=0. Thereafter, a first off-period $t_{OFF}1$ follows. Then, the pattern is repeated with a second on-period $t_{ON}2$, a second off-period $t_{OFF}2$, and so on.

As can be seen in the diagram of FIG. 4, the on- and off-periods $t_{ON}1$, $t_{ON}2$ and $t_{OFF}1$, $t_{OFF}2$ respectively need not have equal extension in time. Preferably, the duration of each on- and off-period $t_{ON}1$, $t_{ON}2$ and $t_{OFF}1$, $t_{OFF}2$ is variable in response to the control signal $C_{ILL}$. Thereby, the emission of light can be optimized with respect to the operation of the at least one imaging device 150.

According to one preferred embodiment of the invention, the processing unit 170 is adapted to receive an input parameter $P_{ON-OFF}$ (see FIG. 1), and in response thereto set the on- and off-periods $t_{ON}1$, $t_{ON}2$ and $t_{OFF}1$, $t_{OFF}2$ respectively of the control signal $C_{ILL}$. Hence, the on-periods $t_{ON}1$ and $t_{ON}2$ can be timed, such that these periods are synchronized with the exposures of the at least one imaging device 150. Namely thereby, the emitted light power can be utilized optimally. Generally, it is further advantageous to set the respective duration of the on-periods $t_{ON}1$ and $t_{ON}2$ to values being shorter than, or equal to, an exposure time of the at least one imaging device 150 because any light energy emitted during the non-exposure periods cannot be used by the imaging device 150.

To further enhance the performance of the proposed system, the light emitting elements of the light source 140 may be controllable in response to the control signal $C_{ILL}$, such that the intensity $I_L$ is variable depending on the characteristics of the control signal $C_{ILL}$. Preferably, the control signal $C_{ILL}$ specifies a light intensity parameter $I_L$ designating a power of the light L to be emitted during the on-period $t_{ON}$. The light intensity parameter $I_L$ may either represent a constant value $i_L$ throughout the on-period $t_{ON}$, as is illustrated in FIG. 4, or the parameter $I_L$ may prescribe a particular variation of the intensity $i_L$ during the on-period $t_{ON}$, e.g. a gradual increase or a pulse width modulation.

Figure 5:
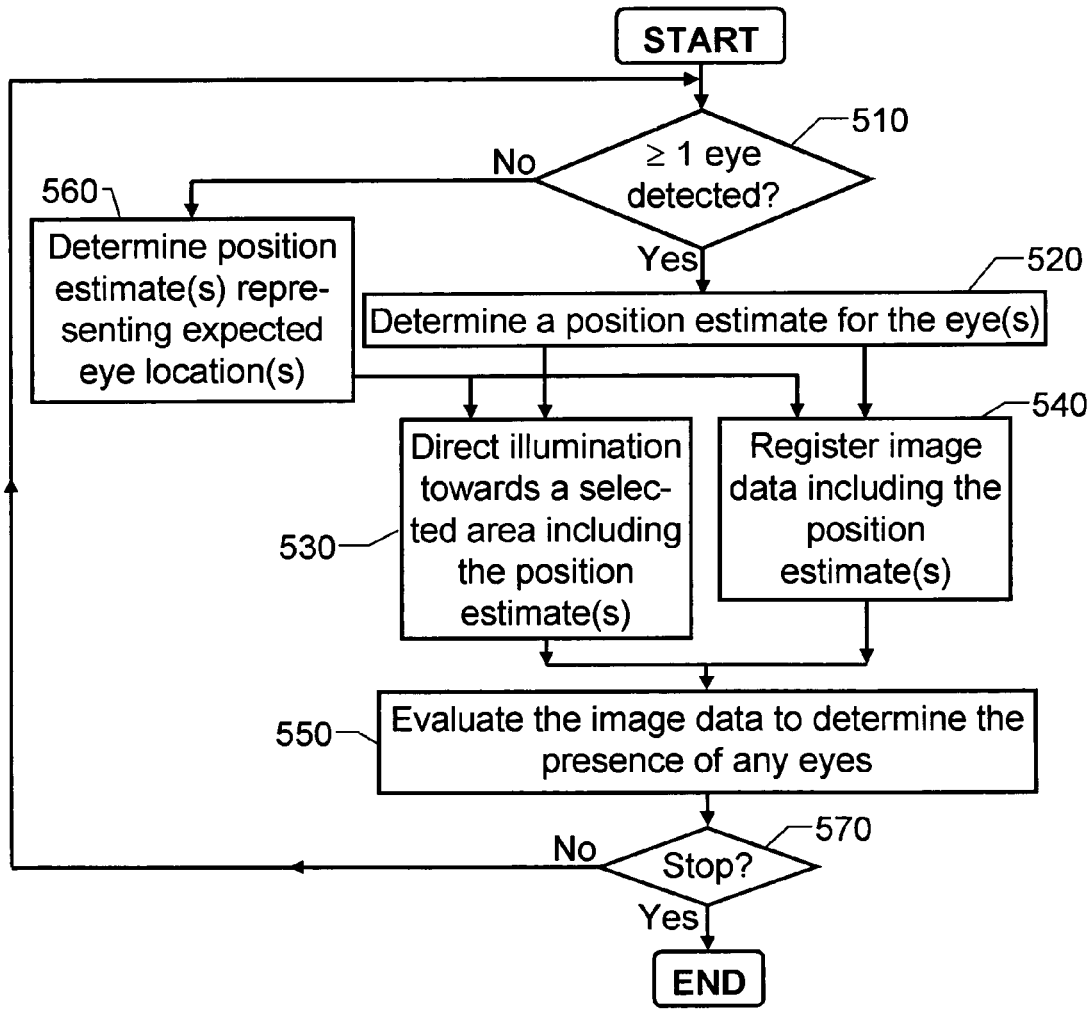
FIG. 5 illustrates, by means of a flow diagram, a general eye-tracking method according to the invention.

To sum up, the general method of controlling an eye-tracking system according to the invention will now be described with reference to the flow diagram in FIG. 5.

An initial step 510 checks whether or not at least one eye of a subject have been detected in the sequential image data registered by the imaging device. If it is found that one or more eyes are detected, a step 520 follows. If however, no eyes are detected, the procedure continues to a step 560.

The step 520 determines a position estimate of each of the at least one eye based on the image data. Preferably, the processing unit here applies conventional eye-tracking algorithms to derive the position estimate(s).

Subsequently, a step 530 illuminates the subject 180 by means of at least one light source. This involves directing at least one light beam towards an illumination area, which includes the position estimate(s). A step 540, likewise subsequent to the step 520 and preferably executed in parallel with the step 530, Registers image data that includes the position estimate(s).

After the steps 530 and 540, a step 550 follows, which evaluates the image data registered in step 540 to determine whether any data representing eyes are present in the image data. Also in step 550, the processing unit preferably applies conventional eye-tracking algorithms.

Thereafter, a step 570 checks whether a stop criterion is fulfilled, e.g. if a given user-command has been received. If the stop criterion is found to be fulfilled, the procedure ends. Otherwise, the procedure loops back to the step 510.

The step 560 determines at least one position estimate for at least one eye based on previously registered images of at least one of the subject's eye. This estimate is preferably determined by the processing unit by extrapolating a movement vector from previously registered images wherein the at least one eye is present. After step 560, the procedure continues to the above-mentioned steps 530 and 540.

All of the process steps, as well as any sub-sequence of steps, described with reference to the FIG. 5 above may be controlled by means of a programmed computer apparatus. Moreover, although the embodiments of the invention described above with reference to the drawings comprise computer apparatus and processes performed in computer apparatus, the invention thus also extends to computer programs, particularly computer programs on or in a carrier, adapted for putting the invention into practice. The program may be in the form of source code, object code, a code intermediate source and object code such as in partially compiled form, or in any other form suitable for use in the implementation of the process according to the invention. The program may either be a part of an operating system, or be a separate application. The carrier may be any entity or device capable of carrying the program. For example, the carrier may comprise a storage medium, such as a Flash memory, a ROM (Read Only Memory), for example a CD (Compact Disc) or a semiconductor ROM, an EPROM (Erasable Programmable Read-Only Memory), an EEPROM (Electrically Erasable Programmable Read-Only Memory), or a magnetic recording medium, for example a floppy disc or hard disc. Further, the carrier may be a transmissible carrier such as an electrical or optical signal which may be conveyed via electrical or optical cable or by radio or by other means. When the program is embodied in a signal which may be conveyed directly by a cable or other device or means, the carrier may be constituted by such cable or device or means. Alternatively, the carrier may be an integrated circuit in which the program is embedded, the integrated circuit being adapted for performing, or for use in the performance of, the relevant processes.

The term "comprises/comprising" when used in this specification is taken to specify the presence of stated features, integers, steps or components. However, the term does not preclude the presence or addition of one or more additional features, integers, steps or components or groups thereof.

The reference to any prior art in this specification is not, and should not be taken as, an acknowledgement or any suggestion that the referenced prior art forms part of the common general knowledge in Australia.

The invention is not restricted to the described embodiments in the figures, but may be varied freely within the scope of the claims.

The invention claimed is:

1. A system for automatically registering and tracking a respective position of at least one eye (181; 182) of a subject (180), comprising:
   at least one imaging device (150) adapted to register sequential image data ($D_{EYE}$) representing the at least one eye (181; 182),
   at least one light source (140) arranged to illuminate the subject (180), each of the at least one light source (140) having a well-defined position relative to the imaging device (150),
   the at least one light source (140) is adapted to:
      vary a spatial location of an illumination area ($A_{ILL}$) towards which at least one light beam (L) from the at least one light source (140) is directed,
      receive a control signal ($C_{ILL}$), and
      direct the at least one light beam (L) towards an illumination area ($A_{ILL}$) specified by the control signal ($C_{ILL}$), and
   a processing unit (170) adapted to receive the image data ($D_{EYE}$), and based thereon produce a position estimate of the at least one eye (181; 182), wherein the processing unit (170) is adapted to produce the control signal ($C_{ILL}$) based on the position estimate of the at least one eye (181; 182) such that the illumination area ($A_{ILL}$) includes the position estimate.

2. The system according to claim 1, wherein the at least one light source (140) comprises a plurality of light emitting elements (241, 241a, 242) being individually controllable in response to the control signal ($C_{ILL}$).

3. The system according to claim 2, wherein the light emitting elements (241, 241a, 242) are arranged in an array (240) comprising a first number ($\#_R$) of rows of elements (241) and a second number ($\#_c$) of columns of elements (241).

4. The system according to claim 2, wherein the at least one light source (140) comprises at least one collimating lens element (310) adapted to influence the light (L) emitted from the light emitting elements such that the light emitted from a first element (241) is directed towards a first portion (A1) of the illumination area ($A_{ILL}$) and the light emitted from a second element (242) is directed towards a second portion (A2) of the illumination area ($A_{ILL}$).

5. The system according to claim 2, wherein the light emitting elements (241) are arranged with different orientations relative to one another, such that a first element (241a) has a first principal light emitting axis (A) having a first angle (α) in a first dimension towards a normal plane (N) of the array (240), and a second element (241) has a second principal light emitting axis whose angle towards the normal plane (N) is different from the first angle (α) at least in the first dimension.

6. The system according to claim 1, wherein the at least one light source (340) is tiltable around at least one axis in response to the control signal ($C_{ILL}$) such that the illumination area ($A_{ILL}$) is adjustable in at least one dimension.

7. The system according to claim 1, wherein the at least one light source (340) is configured to emit light (L) towards at least one mirror (345) being tiltable around at least one axis in response to the control signal ($C_{ILL}$) such that the illumination area ($A_{ILL}$) is adjustable in at least one dimension.

8. The system according to claim 1, wherein the control signal ($C_{ILL}$) is adapted to specify at least one on-period ($t_{ON}1$, $t_{ON}2$) during which light (L) shall be emitted and at least one off-period ($t_{OFF}1$, $t_{OFF}2$) during which no light shall be emitted from a respective at least one light emitting element (241, 241a, 242) of the at least one light source (140, 340).

9. The system according to claim 8, wherein the processing unit (170) is adapted to receive an input parameter ($P_{ON-OFF}$), and in response thereto set the on-and-off-periods ($t_{ON}1$, $t_{ON}2$; $t_{OFF}1$, $t_{OFF}2$) of the control signal ($C_{ILL}$).

10. The system according to claim 1, wherein each of at least one light emitting element (241, 241a, 242) of the at least one light source (140, 340) is controllable in response to the control signal ($C_{ILL}$) such that an intensity ($I_L$) of the light (L) emitted from a given element is variable depending on the characteristics of the control signal ($C_{ILL}$).

11. The system according to claim 10, wherein the control signal ($C_{ILL}$) specifies a light intensity parameter ($I_L$) designating a power of the light (L) to be emitted during the on-period ($t_{ON}$).

12. The system according to claim 11, wherein the light intensity parameter ($I_L$) represents a constant value ($i_L$) throughout the on-period ($t_{ON}$).

13. A method of automatically registering and tracking a respective position of at least one eye (181; 182) of a subject (180), comprising:
registering sequential image data ($D_{EYE}$) by means of at least one imaging device (150), the sequential image data ($D_{EYE}$) representing the at least one eye (181; 182),
illuminating the subject (180) by means of at least one light source (140) having a well-defined position relative to the imaging device (150), the at least one light source (140) being adapted to vary a spatial location of an illumination area ($A_{ILL}$) towards which at least one light beam (L) from the at least one light source (140) is directed,
producing, by means of a processing unit (170), a position estimate of the at least one eye (181; 182) based on the image data ($D_{EYE}$),
receiving a control signal ($C_{ILL}$),
directing the at least one light beam (L) from the at least one light source (140) towards an illumination area ($A_{ILL}$) in response to the control signal ($C_{ILL}$),
producing, by means of a processing unit (170), a position estimate of the at least one eye (181; 182) based on the image data ($D_{EYE}$), and
producing the control signal ($C_{ILL}$) in the processing unit (170) based on the position estimate of the at least one eye (181; 182) such that the illumination area ($A_{ILL}$) includes the position estimate.

14. The method according to claim 13, wherein the control signal ($C_{ILL}$) specifying at least one on-period ($t_{ON}1$, $t_{ON}2$) during which light (L) shall be emitted and at least one off-period ($t_{OFF}1$, $t_{OFF}2$) during which no light shall be emitted from a respective at least one light emitting element (241, 241a, 242) of the at least one light source (140, 340).

15. The method according to claim 13, wherein receiving an input parameter ($P_{ON-OFF}$), and in response thereto setting the on- and off-periods ($t_{ON}1$, $t_{ON}2$; $t_{OFF}1$, $t_{OFF}2$) of the control signal ($C_{ILL}$).

16. The method according to claim 13, further comprising controlling each of at least one light emitting element (241, 241a, 242) of the at least one light source (140, 340) in response to the control signal ($C_{ILL}$) such that an intensity ($I_L$) of the light (L) emitted from a given element is varies depending on the characteristics of the control signal ($C_{ILL}$).

17. The method according to claim 16, wherein the control signal ($C_{ILL}$) specifies a light intensity parameter ($I_L$) designating a power of the light (L) to be emitted during the on-period ($t_{ON}$).

18. The method according to claim 17, wherein the light intensity parameter ($I_L$) represents a constant value ($i_L$) throughout the on-period ($t_{ON}$).

19. A computer program stored on a non-transitory computer readable medium comprising:
an executable portion configured for registering sequential image data ($D_{EYE}$) by means of at least one imaging device (150), the sequential image data ($D_{EYE}$) representing the at least one eye (181; 182),
an executable portion configured for illuminating the subject (180) by means of at least one light source (140) having a well-defined position relative to the imaging device (150), the at least one light source (140) being adapted to vary a spatial location of an illumination area ($A_{ILL}$) towards which at least one light beam (L) from the at least one light source (140) is directed,
an executable portion configured for receiving a control signal ($C_{ILLL}$),
an executable portion configured for directing the at least one light beam (L) from the at least one light source (140) towards an illumination area ($A_{ILL}$) in response to the control signal ($C_{ILL}$),
an executable portion configured for producing, by means of a processing unit (170), a position estimate of the at least one eye (181; 182) based on the image data ($D_{EYE}$), and
an executable portion configured for producing the control signal ($C_{ILL}$) in the processing unit (170) based on the position estimate of the at least one eye (181; 182) such that the illumination area ($A_{ILL}$) includes the position estimate.

20. A non-transitory computer readable storage medium (175), having a program recorded thereon, where the program comprises
an executable portion configured for registering sequential image data ($D_{EYE}$) by means of at least one imaging device (150), the sequential image data ($D_{EYE}$) representing the at least one eye (181; 182),
an executable portion configured for illuminating the subject (180) by means of at least one light source (140) having a well-defined position relative to the imaging device (150), the at least one light source (140) being adapted to vary a spatial location of an illumination area ($A_{ILL}$) towards which at least one light beam (L) from the at least one light source (140) is directed,
an executable portion configured for receiving a control signal ($C_{ILL}$),
an executable portion configured for directing the at least one light beam (L) from the at least one light source (140) towards an illumination area ($A_{ILL}$) in response to the control signal ($C_{ILL}$), an executable portion configured for producing, by means of a processing unit (170), a position estimate of the at least one eye (181; 182) based on the image data ($D_{EYE}$), and an executable portion configured for producing the control signal ($C_{ILL}$) in the processing unit (170) based on the position estimate of the at least one eye (181; 182) such that the illumination area ($A_{ILL}$) includes the position estimate.

\* \* \* \* \*